US009027184B2

(12) United States Patent
Cohen (10) Patent No.: US 9,027,184 B2
(45) Date of Patent: May 12, 2015

(54) ACUPRESSURE PILLOWS

(71) Applicant: Steven M. Cohen, Arlington, VA (US)

(72) Inventor: Steven M. Cohen, Arlington, VA (US)

(*) Notice: Subject to any disclaimer, the term of this patent is extended or adjusted under 35 U.S.C. 154(b) by 0 days.

(21) Appl. No.: 13/803,345

(22) Filed: Mar. 14, 2013

(65) Prior Publication Data

US 2014/0259422 A1    Sep. 18, 2014

(51) Int. Cl.
*A47G 9/10* (2006.01)
*A61F 5/00* (2006.01)

(52) U.S. Cl.
CPC .............. *A47G 9/10* (2013.01); *A47G 9/1081* (2013.01); *A61F 5/00* (2013.01); *Y10S 5/944* (2013.01)

(58) Field of Classification Search
CPC ............ A61H 2015/00; A61H 2015/0007; A61H 2015/0064; A47G 9/10
USPC ............ 5/630–633, 636, 639, 643, 655.9, 5/657.5, 948, 640, 642, 657; 601/57; 297/284.8
See application file for complete search history.

(56) References Cited

U.S. PATENT DOCUMENTS

| | | | |
|---|---|---|---|
| 1,326,875 A | 12/1919 | Miller | |
| 2,667,869 A | 2/1954 | D'Elia | |
| 3,981,032 A * | 9/1976 | Brooks | 5/639 |
| 4,488,315 A | 12/1984 | Hoerlein | 2/91 |
| 4,524,464 A | 6/1985 | Primiano et al. | 2/161 A |
| 4,683,601 A | 8/1987 | Lagin | 5/431 |
| 4,771,493 A * | 9/1988 | Park | 5/637 |
| 4,796,616 A * | 1/1989 | Panahpour | 601/131 |
| 4,974,582 A * | 12/1990 | Johnson | 601/134 |
| 5,481,771 A * | 1/1996 | Burk, IV | 5/636 |
| 5,577,995 A * | 11/1996 | Walker et al. | 601/120 |
| 5,577,996 A * | 11/1996 | Gardner et al. | 601/120 |
| 5,787,541 A * | 8/1998 | Chen | 15/222 |
| 5,864,903 A | 2/1999 | Newman | 5/639 |
| 5,878,438 A | 3/1999 | Ragsdale | 2/158 |
| 6,007,501 A * | 12/1999 | Cabados et al. | 601/15 |
| 6,024,762 A * | 2/2000 | Gray | 607/109 |
| 6,174,297 B1 * | 1/2001 | Chen | 601/128 |
| 6,182,313 B1 * | 2/2001 | Eschenbach | 5/640 |
| 6,305,040 B1 | 10/2001 | Myler | 5/636 |
| 6,463,608 B1 | 10/2002 | Moe | 5/646 |
| 6,526,612 B1 | 3/2003 | Zarrella | 5/636 |
| 6,851,146 B1 | 2/2005 | Kristof et al. | 5/636 |
| 7,452,339 B2 * | 11/2008 | Mattison | 601/15 |
| 7,811,241 B1 * | 10/2010 | Baker | 601/131 |
| 8,156,939 B1 * | 4/2012 | Maddalena | 128/845 |
| 2003/0144616 A1* | 7/2003 | Henderson | 601/131 |
| 2004/0243035 A1* | 12/2004 | Devlin | 601/131 |
| 2007/0055187 A1* | 3/2007 | Magnone et al. | 601/132 |

(Continued)

*Primary Examiner* — Nicholas Polito
*Assistant Examiner* — David R Hare
(74) *Attorney, Agent, or Firm* — Sunstein Kann Murphy & Timbers LLP (57) ABSTRACT

An acupressure pillow includes pressure members that are interconnected by an elastic member and arranged so that, when the user rests a body part (e.g., head or neck) on the pillow between the pressure members, the pressure members automatically adjust to accommodate the body part and produce pressure on the body part due at least in part to the elastic member, which biases the pressure members toward one another. Thus, the pressure exerted on the body part may have different vector components, including some pressure produced essentially perpendicular to the pillow surface on which the body part rests and some pressure produced at other angles due to the shape of the pressure members and the inward force on the pressure members produced by the elastic member.

16 Claims, 10 Drawing Sheets

(56) References Cited

U.S. PATENT DOCUMENTS

| | | | |
|---|---|---|---|
| 2008/0172793 A1 | 7/2008 | Gagneur et al. | 5/646 |
| 2008/0189863 A1 | 8/2008 | Zappas | 5/636 |
| 2008/0271742 A1 | 11/2008 | Maginness | 128/845 |
| 2009/0131973 A1* | 5/2009 | Zacharias | 606/204 |
| 2009/0250069 A1 | 10/2009 | Frey | 128/845 |
| 2010/0094333 A1* | 4/2010 | Akcasu | 606/204 |
| 2012/0053618 A1 | 3/2012 | Sorensen | 606/204 |
| 2013/0085426 A1* | 4/2013 | Brodsky | 601/128 |

* cited by examiner

ACUPRESSURE PILLOWS

FIELD OF THE INVENTION

The present invention relates generally to an acupressure pillow such as to provide pressure or massage to reduce headaches.

BACKGROUND OF THE INVENTION

Headaches and migraine headaches are very common. Headaches have been written about since the time of the Babylonians and migraine headaches are even discussed in the bible. People often experience headaches and migraines during times of increased emotional or physical stress.

SUMMARY OF EXEMPLARY EMBODIMENTS

In one embodiment there is provided an acupressure pillow comprising a cushion material and at least one pressure assembly disposed within the cushion material, wherein each pressure assembly comprises a pair of pressure members movably interconnected by an elastic member.

In another embodiment there is provided a pressure assembly for an acupressure pillow, the pressure assembly comprising a pair of pressure members movably interconnected by an elastic member.

In various alternative embodiments, the cushion material may be a memory foam material or other type of cushion material. In some embodiments, the pressure members are spherical, while in other embodiments, the pressure members are non-spherical (e.g., oblong or hemispherical). In some embodiments, the pressure members are substantially the size, shape, material, and firmness of a tennis ball. In some embodiments, the pressure members are solid, while in other embodiments, the pressure members are hollow. The elastic member may be any suitable elastic member such as, for example, a tension spring or elastic band.

Typically, the pressure members are maintained a predetermined minimum distance apart from one another, such as by a spacer block disposed between the pressure members, a portion of the cushion material, the elastic member, and/or a guide. Certain embodiments additionally include a guide that restricts movement of the pressure members of a pressure assembly in at least one direction. The guide may comprise a track, such as a linear flat track, a curved flat track, or an upwardly curved track.

In some embodiments, the pressure members are placed such that a portion of each pressure member extends above a nominal top surface of the cushion material, while in other embodiments, the pressure members are placed such that no portion of the pressure members extends above the nominal top surface of the cushion material. A pressure assembly may be removably installed in the cushion material, e.g., to allow for removal of the pressure assembly such as for heating, cooling, cleaning, or maintenance.

Certain embodiments include a plurality of pressure assemblies. In such embodiments, all of the pressure assemblies may have the same size/type of pressure members, or, in some cases, at least two pressure assemblies may have different sized pressure members. In such embodiments, all of the pressure assemblies may be placed at the same depth relative to a surface of the cushion material, or, in some cases, at least two pressure assemblies may be placed at different depths relative to a surface of the cushion material.

Additional embodiments may be disclosed and claimed.

BRIEF DESCRIPTION OF THE DRAWINGS

The foregoing features of embodiments will be more readily understood by reference to the following detailed description, taken with reference to the accompanying drawings, in which.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Definitions. As used in this description and the accompanying claims, the following terms shall have the meanings indicated, unless the context otherwise requires:

A "pillow" is any of a variety of cushions that can support the head, neck, and optionally other body part(s) of a user. A pillow may be a stand-alone product (e.g., a pillow of the type typically used for sleeping) or may be attached to or integral with another product (e.g., the headrest of a chair or table such as a lounge chair, massage chair, massage table, automobile seat, airline seat, etc.).

The term "movably interconnected" with regard to two pressure members means that the pressure members are interconnected in such a way that one, the other, or both pressure members can move relative to the other pressure member.

In embodiments of the present invention, a pillow includes pressure members that are interconnected by an elastic member and arranged so that, when the user rests a body part (e.g., head or neck) on the pillow between the pressure members, the pressure members automatically adjust to accommodate the body part and produce pressure on the body part due at least in part to the elastic member, which biases the pressure members toward one another. Thus, the pressure exerted on the body part may have different vector components, including some pressure produced essentially perpendicular to the pillow surface on which the body part rests and some pressure produced at other angles due to the shape of the pressure members and the inward force on the pressure members produced by the elastic member.

In specific embodiments, the acupressure pillow may be configured specifically to provide pressure designed to decrease pain associated with stress headaches, e.g., to slightly increase pressure to the base of the cranium at the foramen magnum. This is the location where the spinal cord and brain stem join. This is also the same location as the cervical spine vertebrae C1-C7 and nerve pairs C-1 through C-8 are located. At this point, there is a formation of an extensive network of nerve groups attaching to the spinal cord called Rami or Plexus. When a person is under stress, this area often is tightened by muscles, which in turn can block normal flow of blood and nerve receptors, both sensory and motor nerves. The pressure placed on the muscles by use of this pillow may loosen the muscles and hence may increase blood flow back to the brain, receptors and sensory and motor nerves, thereby reducing the headache. Additionally, the pressure obtained into the neck from the pillow may also increase blood flow to the Brachial plexus, which provides the nerve supply to the shoulder and upper limbs.

Figure 1:
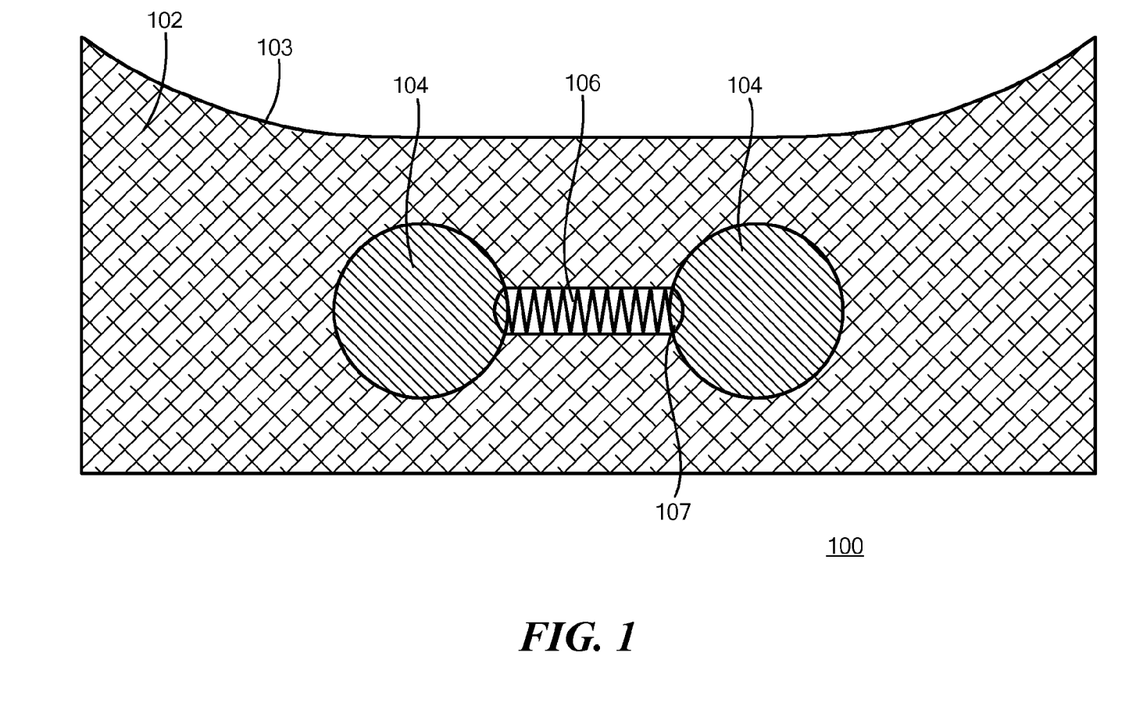
FIG. 1 is a schematic cross-sectional diagram of an acupressure pillow, in accordance with one exemplary embodiment.

FIG. 1 is a schematic cross-sectional diagram of an acupressure pillow 100, in accordance with one exemplary embodiment. The pillow 100 includes one or more pressure assemblies (one shown here) disposed in the cushion material 102 of the pillow 100, where each pressure assembly includes a pair of pressure members 104 (shown here as spheres, although alternative shapes are possible as discussed below) interconnected by an elastic member 102 (shown here as a spring, although alternative elastic members are possible as discussed below). The elastic member 106 attaches to the pressure members 104 by an appropriate attachment mechanism 107. As discussed further below, the pressure members 104 are nominally spaced by a predetermined distance, for example, using a spacer block, the cushion material 102, the elastic member 106, or other spacer element. The cushion material 102 may be any of a variety of materials generally used for pillows (e.g., foam, memory foam, feathers, synthetic fibers, pellets, microbeads, beanbag filler, etc.). In one specific exemplary embodiment, the cushion material 102 is a soft high-grade memory foam. The cushion material 102 may be held in place or otherwise covered with a covering 103 (e.g., cloth or other thin material).

Figure 2:
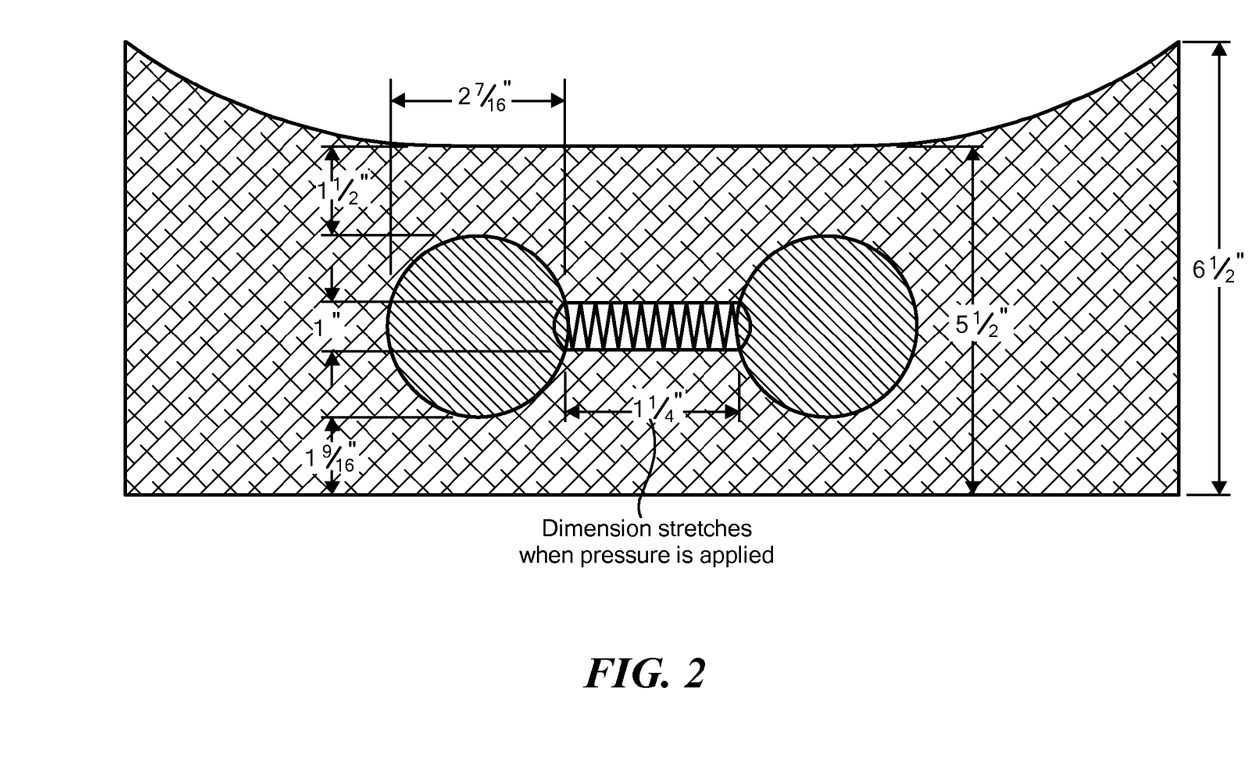
FIG. 2 shows various approximate dimensions for but one specific implementation of the acupressure pillow shown in FIG. 1.

FIG. 2 shows various approximate dimensions for but one specific implementation of the acupressure pillow shown in FIG. 1. Here, the pressure members 104 are spherical and are substantially the size of standard tennis balls (and, in fact, tennis balls may be used as the pressure members in certain embodiments). The pressure members are nominally 1.25" apart but separate further when pressure is applied by a body part resting on the pillow, and hence the elastic member 106 stretches and applies an inward force on the pressure members which in turn apply an inward force on the body part, in addition to the nominal force(s) applied on the body part by simply resting on the pillow about the pressure members (e.g., forces perpendicular to the pillow surface due to the weight of the body part).

Figure 3:
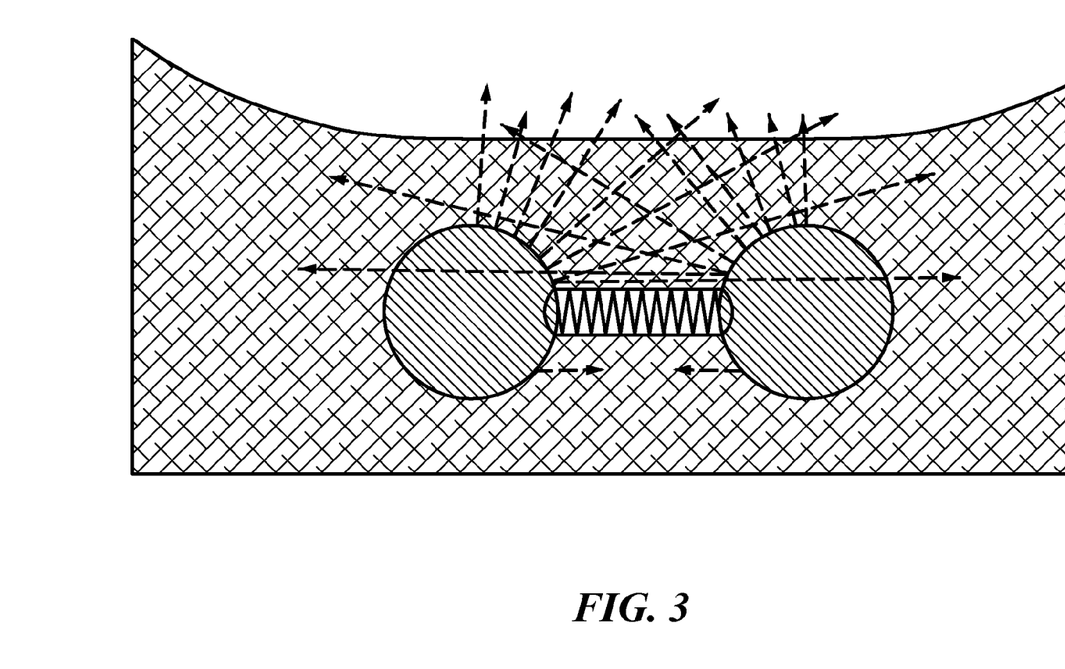
FIG. 3 schematically depicts various vector components produced on a body part by the pressure members and elastic member of FIG. 1.

FIG. 3 schematically depicts various vector components produced on a body part by the pressure members and elastic member of FIG. 1, including some pressure produced essentially perpendicular to the pillow surface on which the body part rests and some pressure produced at other angles due to the shape of the pressure members and the inward force on the pressure members produced by the elastic member.

In various alternative embodiments, the pressure members 104 may be spherical or non-spherical (e.g., oblong, hemispherical, etc.) and may be hollow or solid (in either case, pressure members may be compressible or non-compressible, e.g., certain embodiments may use solid, compressible pressure members while other embodiments may use hollow, non-compressible pressure members).

In a preferred embodiment, the elastic member 106 includes a tension spring or combination of springs (e.g., one spring inside another to provide extra force), although in various alternative embodiments, the elastic member 106 may be another type of suitable elastic member, such, for example, an elastic band or other mechanism. The term "elastic member" may encompass interconnection mechanisms having multiple parts (e.g., a mechanism having springs, gears, cams or other mechanical parts configured to perform the function of an elastic member in the context of the present invention), not just a single element. It should be noted that various alternative embodiments may use elastic members 106 having different spring constants, e.g., weaker for smaller people and stronger for larger people. In some embodiments, the elastic member 106 may be replaceable, in case the elastic member 106 breaks or weakens due to repeated stretching, or in order to use different elastic members for different people who use the acupressure pillow.

In various alternative embodiments, the acupressure pillow 100 may be any of a variety of shapes, such as substantially rectangular, cylindrical, or other pillow shapes. The pillow may include contours (not shown) to provide specific types of support for the body part, such as, for example, raised elements, depressed elements, etc.

In various alternative embodiments, the pressure assembly or assemblies may be installed into the cushion material 102 (e.g., in a cavity or cavities formed in the cushion material 102) or may be molded into the cushion material 102 (e.g., memory foam molded around the pressure assembly.

Figure 4:
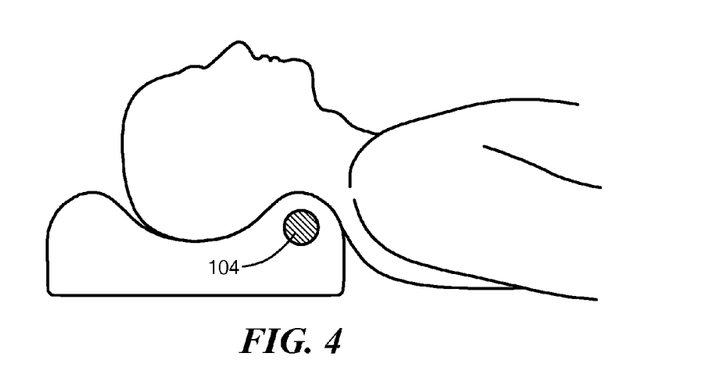
FIG. 4 is a schematic cross-sectional diagram of a person's head and neck resting on a rectangular acupressure pillow, in accordance with one exemplary embodiment.

FIG. 4 is a schematic cross-sectional diagram of a person's head and neck resting on a rectangular acupressure pillow, in accordance with one exemplary embodiment.

Figure 5:
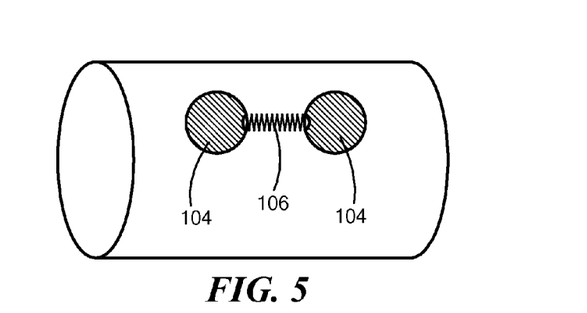
FIG. 5 is a schematic isometric diagram of a cylindrical acupressure pillow, in accordance with another exemplar embodiment.

FIG. 5 is a schematic isometric diagram of a cylindrical acupressure pillow, in accordance with another exemplar embodiment.

Figure 6:
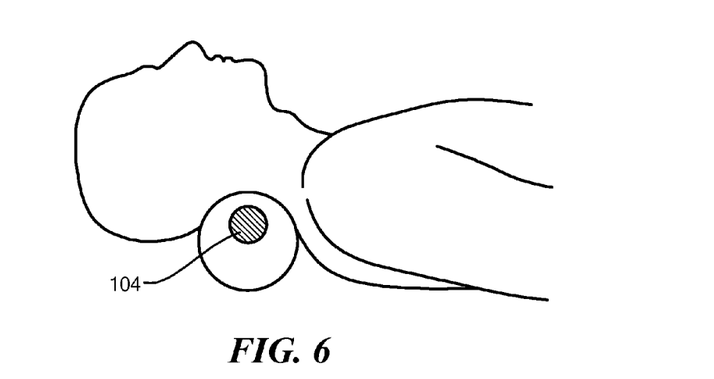
FIG. 6 is a schematic cross-sectional diagram of a person's head and neck resting on a cylindrical acupressure pillow of the type shown in FIG. 5.

FIG. 6 is a schematic cross-sectional diagram of a person's head and neck resting on a cylindrical acupressure pillow of the type shown in FIG. 5.

As discussed above, the pressure members 104 are nominally spaced by a predetermined distance, for example, using a spacer block, the cushion material 102, the elastic member 106 (e.g., a spring generally would provide a nominal spacing equal to the relaxed length of the spring), or other spacer element (e.g., a guide, as discussed below). In some embodiments, a spacer block or other spacer element may be part of the pressure assembly discussed above.

Figure 7:
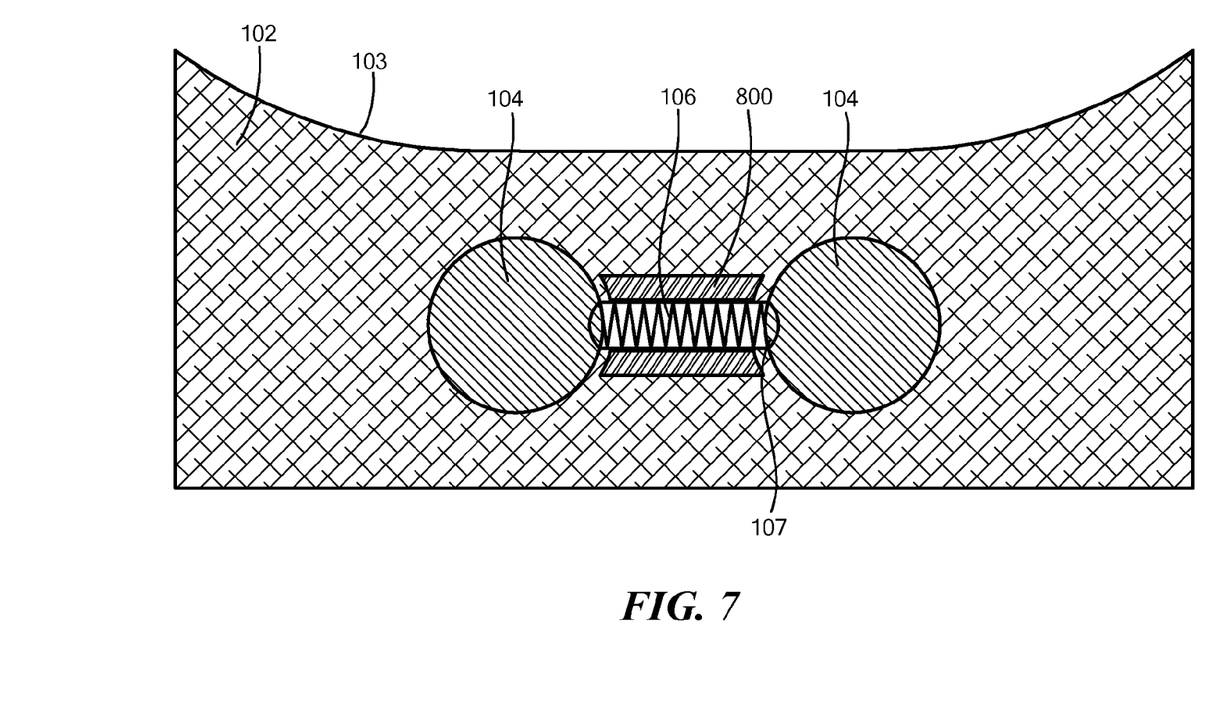
FIG. 7 is a schematic cross-sectional diagram showing an acupressure pillow having a spacer block to provide a nominal spacing between the pressure members, in accordance with one exemplary embodiment.

FIG. 7 is a schematic cross-sectional diagram showing an acupressure pillow having a spacer block 800 to provide a nominal spacing between the pressure members 104, in accordance with one exemplary embodiment. The spacer block 800 may be made from any suitable material, such as, for example, plastic. The spacer block 800 generally would include a space through which the elastic member 106 extends. The relaxed length of the elastic member 106 may be less than the length of the spacer block 800 so that the elastic member 106 provides an inward force on the pressure members 104 when the pressure members 104 are separated by their nominal spacing due to the spacer block 800.

Figure 8:
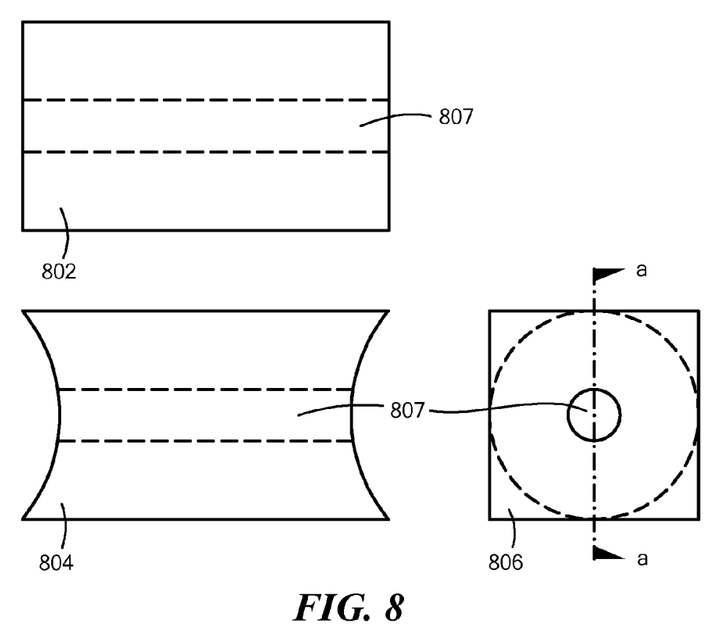
FIG. 8 is a schematic orthographic projection of the spacer block of FIG. 7, in accordance with one exemplary embodiment.

FIG. 8 is a schematic orthographic projection of the spacer block 800 of FIG. 7, in accordance with one exemplary embodiment. Top view 802 shows, by dashed lines, the internal space 107 through which the elastic member 106 extends. End view 806 shows the space 107 as a hole drilled through the spacer block 800 through which the elastic member 106 extends, although the space may be formed in other ways, e.g., as a channel formed in the spacer block 800. View 804 is a cross-sectional view along section a-a in end view 806. The view 804 shows the space 107 as well as the concave shapes of the ends of the spacer block 800 to accommodate spherical pressure members of the type shown in FIG. 1. The end view 806 shows the spacer block 806 as being square, although the spacer block 800 could be other shapes, e.g., cylindrical, as shown by the dashed circle in view 806.

It should be noted that, in some embodiments, the cushion material 102 may provide the nominal spacing for the pressure members, e.g., by leaving cushion material between the pressure members and providing a channel through that portion of cushion material through which the elastic member 106 extends.

Figure 9:
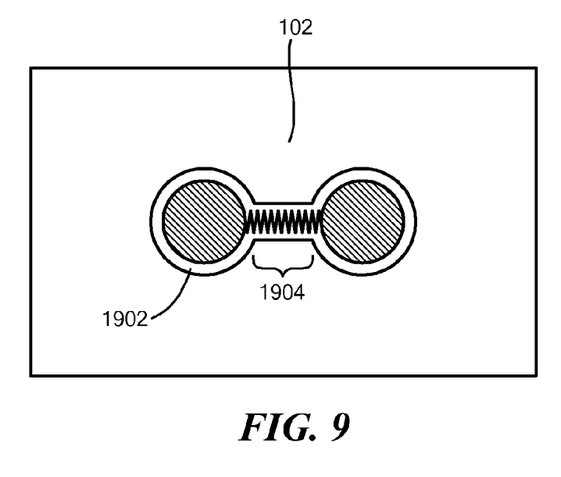
FIG. 9 is a schematic diagram showing a cavity in the cushion material into which is inserted a pressure assembly having a pair of pressure members interconnected by an elastic member, in accordance with one exemplary embodiment.

FIG. 9 is a schematic diagram showing a cavity 1902 in the cushion material 102 into which is inserted a pressure assembly having a pair of pressure members interconnected by an elastic member, in accordance with one exemplary embodiment. A portion of cushion material 1904 acts as the spacer by preventing the pressure members from moving closer to one another than the predetermined nominal spacing. The cavity 1902 includes a channel through which the elastic member extends.

In certain embodiments, the pressure assembly, and specifically the pressure members 104, may be supported solely by the cushion material 102. In other embodiments, however, the pressure members 104 may be supported by a guide, such as, for example a track. Among other things, the guide restricts the movement of the pressure members 104 to certain direction(s). The guide also may provide the nominal spacing for the pressure members by, for example, preventing the pressure members from moving within the predetermined distance from one another. The guide can be virtually any shape suitable for a particular implementation. In some embodiments, the guide may be part of the pressure assembly discussed above.

Figure 10:
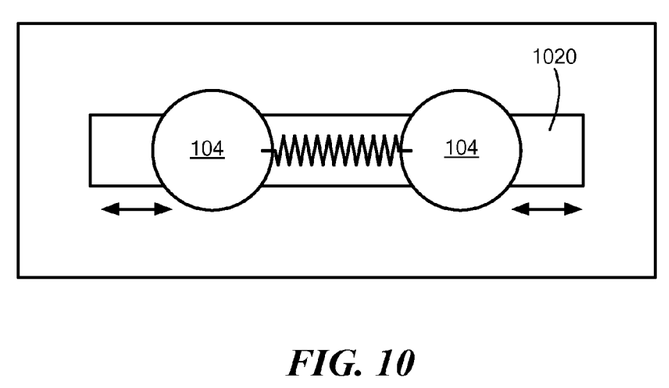
FIG. 10 is a schematic diagram showing a linear flat guide that guides the movement of the pressure members, in accordance with one exemplary embodiment.

FIG. 10 is a schematic diagram showing a linear flat guide 1020 that guides the movement of the pressure members 104, in accordance with one exemplary embodiment.

Figure 11:
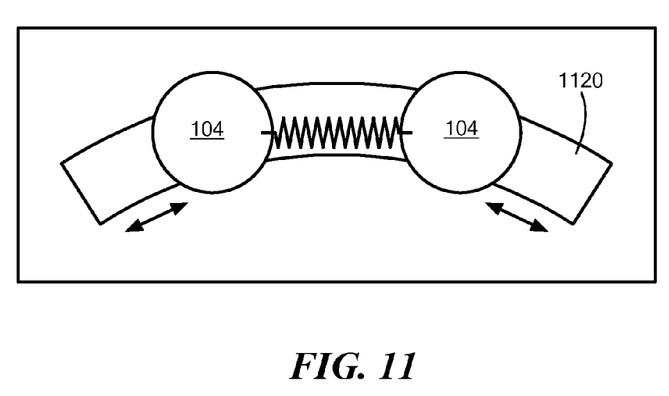
FIG. 11 is a schematic diagram showing a curved flat guide 1120 that guides the movement of the pressure members 104, in accordance with one exemplary embodiment.

FIG. 11 is a schematic diagram showing a curved flat guide 1120 that guides the movement of the pressure members 104, in accordance with one exemplary embodiment.

It should be noted that no spacer is shown in FIGS. 10 and 11, although a spacer may be included and may be attached to or integral to the guide.

Figure 12:
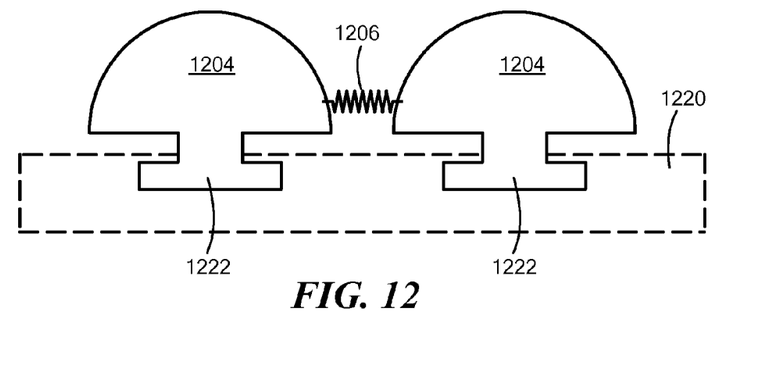
FIG. 12 is a schematic diagram showing alternatively-shaped pressure members interconnected by an elastic member and configured for use with a guide track, in accordance with one exemplary embodiment.

FIG. 12 is a schematic diagram showing alternatively-shaped pressure members 1204 interconnected by an elastic member 1206 and configured for use with a guide track 1220, in accordance with one exemplary embodiment. Here, the pressure members 1204 are hemispherical and include guide pins 1222 that ride within a channel in the guide track 1220.

Figure 13:
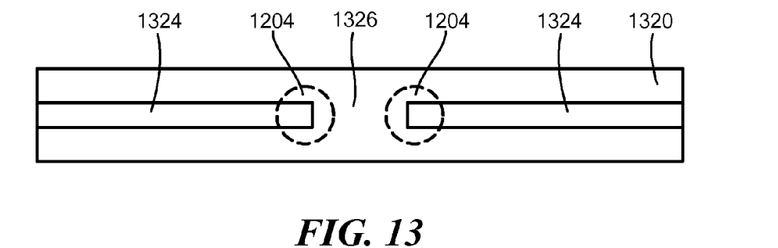
FIG. 13 is a schematic diagram showing a linear guide track of the type discussed with reference to FIG. 10 configured for use with the pressure members shown in FIG. 12, in accordance with one exemplary embodiment.

FIG. 13 is a schematic diagram showing a linear guide track 1320 of the type discussed with reference to FIG. 10 configured for use with the pressure members 1204 shown in FIG. 12, in accordance with one exemplary embodiment. Here, the guide track 1320 includes two channels 1324 within which the members 1204 (shown by dashed lines) ride such that the guide pins 1222 (which are wider than the channels 1324) maintain the pressure members 1204 within the channels 1324. In this example, each guide track 1324 is open at the end of the guide track 1320 to allow a pressure member 1204 to be easily installed in the channel 1324. An area 1326 between the channels 1324 acts as a spacer to provide the nominal spacing for the pressure members 1204.

Figure 14:
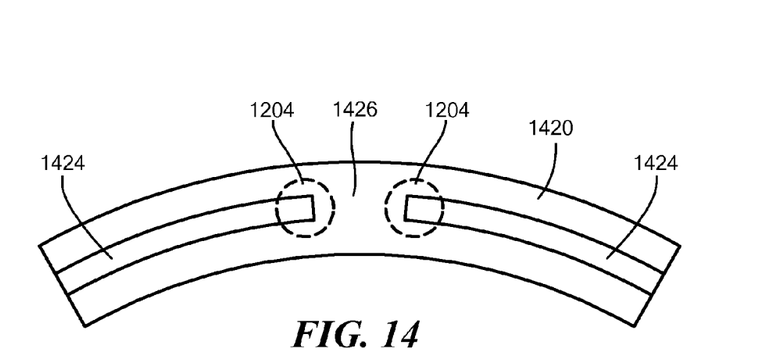
FIG. 14 is a schematic diagram showing a curved guide track of the type discussed with reference to FIG. 11 configured for use with the pressure members shown in FIG. 12, in accordance with one exemplary embodiment.

FIG. 14 is a schematic diagram showing a curved guide track 1420 of the type discussed with reference to FIG. 11 configured for use with the pressure members 1204 shown in FIG. 12, in accordance with one exemplary embodiment. Here, as in FIG. 13, the guide track 1420 includes two channels 1424 within which the members 1204 (shown by dashed lines) ride such that the guide pins 1222 (which are wider than the channels 1424) maintain the pressure members 1204 within the channels 1424. In this example, each guide track 1424 is open at the end of the guide track 1420 to allow a pressure member 1204 to be easily installed in the channel 1424. An area 1426 between the channels 1424 acts as a spacer to provide the nominal spacing for the pressure members 1204.

It should be noted that a guide need not be flat but instead may be curved upward such that the pressure members move vertically as well as horizontally when the body part is rested on the pillow about the pressure members.

Figure 15:
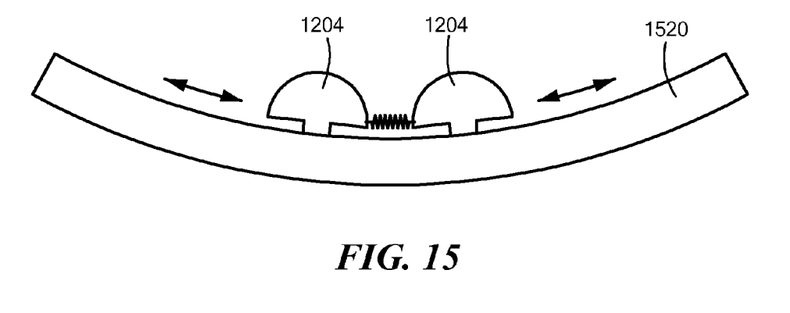
FIG. 15 shows an upwardly-curved guide track for use with the pressure members shown in FIG. 12, in accordance with one exemplary embodiment.

FIG. 15 shows an upwardly-curved guide track 1520 for use with the pressure members 1204 shown in FIG. 12, in accordance with one exemplary embodiment.

Figure 16:
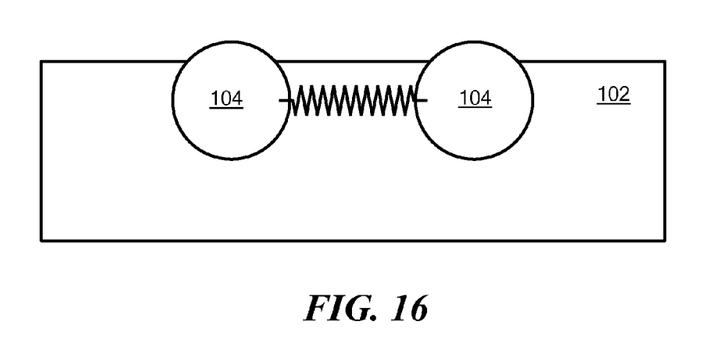
FIG. 16 is a schematic cross-sectional diagram showing pressure members placed such that a portion of each pressure member extends above the nominal top surface of the cushion material, in accordance with one exemplary embodiment.
Figure 17:
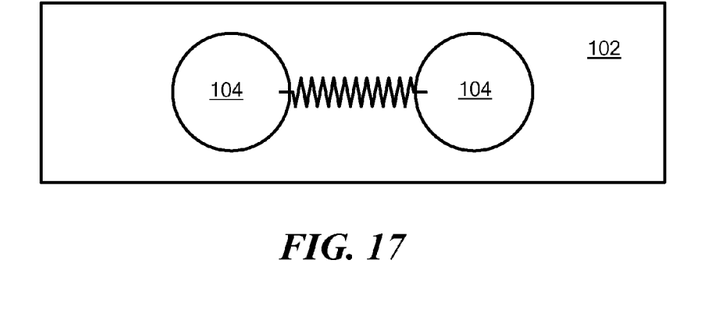
FIG. 17 is a schematic cross-sectional diagram showing pressure members placed such that no portion the pressure members extends above the nominal top surface of the cushion material, in accordance with one exemplary embodiment.

It should be noted that, in any of the above-mentioned embodiments, the pressure members may be placed such that a portion of each pressure member extends above the nominal top surface of the cushion material. FIG. 16 is a schematic cross-sectional diagram showing pressure members placed such that a portion of each pressure member extends above the nominal top surface of the cushion material, in accordance with one exemplary embodiment. Alternatively, the pressure members may be placed such that no portion of the pressure members extends above the nominal top surface of the cushion material. FIG. 17 is a schematic cross-sectional diagram showing pressure members placed such that no portion the pressure members extends above the nominal top surface of the cushion material, in accordance with one exemplary embodiment.

It should be noted that, in any of the above-mentioned embodiments, the maximum distance of travel of the pressure members may be limited so that they cannot separate by more than a predetermined distance, such as, for example, using a flexible fixed-length member attached between the pair of pressure members (e.g., a string or wire that will stop the outward travel of the pressure members), or, in the case of a guide, a block attached to or integral with the guide, or the channel of a guide track, may stop the outward travel of the pressure members. In some cases, the elastic member itself may effectively limit the outward travel of the pressure members during normal use of the product, e.g., the limit on how far the elastic member can stretch. In some cases, the cushion material may effectively limit the outward travel of the pressure members during normal use of the product.

Figure 18:
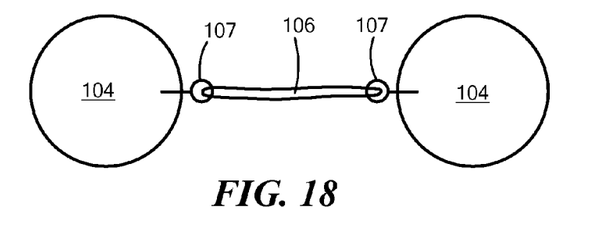
FIG. 18 is a schematic diagram showing the pressure members interconnected by an elastic band attached to the pressure members via screw eye hooks, in accordance with one alternative embodiment.
Figure 20:
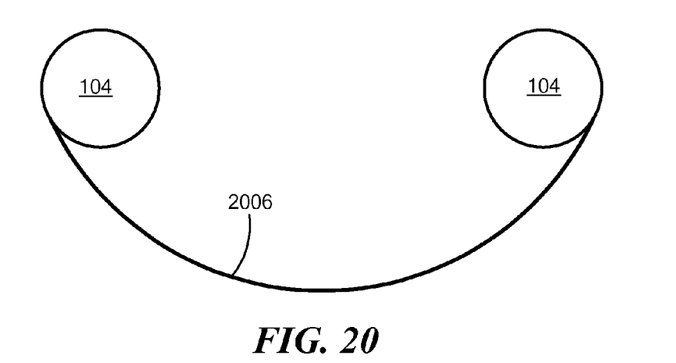
FIG. 20 is a schematic cross-sectional diagram showing pressure members interconnected by an arc-shaped spring, such as, for example, a single length of spring metal or a leaf spring, in accordance with one exemplary embodiment.

As discussed above, many types of elastic members may be used in alternative embodiments of the present invention. FIG. 18 is a schematic diagram showing pressure members 104 interconnected by an elastic band 106 attached to the pressure members 104 via screw eye hooks, in accordance with one alternative embodiment. FIG. 20 is a schematic cross-sectional diagram showing pressure members 104 interconnected by an arc-shaped spring 2006, such as, for example, a single length of spring metal or a leaf spring. In FIG. 20, the pressure members 104 are affixed to the spring 2006 toward the ends of the spring (e.g., by pressure fit, glue, mechanical fastener, etc.), and the spring 2006 allows the pressure members 104 to move apart from one another when the body part is rested on the pillow about the pressure members 104 and brings the pressure members 104 back to their original position when the body part is removed. Other types of elastic members are possible within the scope of the present invention.

Figure 19:
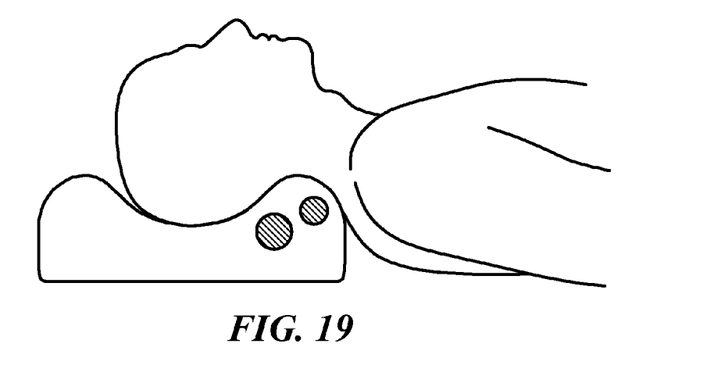
FIG. 19 is a schematic cross-sectional diagram showing multiple pairs of pressure members of different sizes placed at different relative heights, in accordance with one exemplary embodiment.

It should be noted that various alternative embodiments may include multiple pairs of interconnected pressure members (e.g., multiple pressure member assemblies). For example, a particular embodiment might include two, three, four, or more pairs of interconnected pressure members so as to place pressure on different points of the body part. In such embodiments, different pairs of interconnected pressure members may be placed at different relative depths (e.g., as depicted schematically in FIG. 19) and/or may have different configurations, e.g., different size pressure members (also as depicted schematically in FIG. 19), different types or shapes of pressure members (e.g., different pairs may have pressure members of different hardness levels), elastic members of different spring constants, different nominal distances between pressure members (e.g., pressure members for a neck might have a smaller nominal distance that pressure members for a head), etc.

It should be noted that, in various alternative embodiments, the cushion material and/or the pressure members may be configured to provide additional stimuli, such as, for example, heating, cooling, massage (e.g., vibration), or other stimuli. Certain stimuli may be provided electronically, e.g., by including an electronic heating element or massager. Alternatively, heat and/or cold may be provided by allowing the pressure assembly to be removed from the pillow, and placed in a heater (e.g., oven) or cooler (e.g., refrigerator or freezer), and then replaced in the pillow. Such removal/replacement of the pressure assembly also may allow for cleaning and/or maintenance of the pressure assembly (e.g., changing pressure members and/or the elastic member, such as for repair of the pressure assembly or reconfiguration of the pressure assembly for different users).

In various alternative embodiments, various other types of elements may be included in the pillow, e.g., in the cushion material or as part of the pressure assembly, such as, for example, speakers through which music or other audio can be played, additional massage elements (e.g., fixed or movable elements), one or more pockets to hold hot/cold packs, adjustable pillow firmness, areas of different pillow firmness, and/or other types of elements. The cushion material may be configured to provide a rest or guide for the body part(s) to help position body part(s) about the pressure elements, e.g., a headrest element including a U-shaped or V-shaped depression in the cushion material to help position the head and/or neck about the pressure members.

It should be noted that, in some cases, pressure assemblies of the type described herein may be provided or sold separately from the remainder of the pillow and hence such pressure assemblies constitute certain embodiments of the present invention.

It should be noted that, in some cases, certain products (e.g., a chair or table such as a lounge chair, massage chair, massage table, automobile seat, airline seat, etc.) may include, or be configured to accept, pillows and/or pressure assemblies of the types described herein and hence such products constitute certain embodiments of the present invention.

The present invention may be embodied in other specific forms without departing from the true scope of the invention, and numerous variations and modifications will be apparent to those skilled in the art based on the teachings herein. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. An acupressure pillow configured to support at least one body part of a user; the acupressure pillow comprising:
   a cushion material; and
   at least one pressure assembly disposed within the cushion material and configured to provide acupressure to said at least one body part of the user, wherein each pressure assembly comprises a pair of pressure members for providing such acupressure, the pair of pressure members movably interconnected by an elastic member that is attached to the pressure members such that the pressure members are biased toward one another, each pressure assembly further including a spacer to provide a nominal spacing between the pressure members, wherein a relaxed length of the elastic member is less than the nominal spacing between the pressure members so that the elastic member provides an inward force on the pressure members when the pressure members are separated by their nominal spacing due to the spacer.

2. An acupressure pillow according to claim 1, wherein the cushion material is a memory foam material.

3. An acupressure pillow according to claim 1, wherein the pressure members of a pressure assembly are spherical.

4. An acupressure pillow according to claim 1, wherein the pressure members of a pressure assembly are substantially the size, shape, material, and firmness of a tennis ball.

5. An acupressure pillow according to claim 1, wherein the pressure members of a pressure assembly are hollow.

6. An acupressure pillow according to claim 1, wherein the elastic member of a pressure assembly includes at least one of:
   a tension spring; or
   an elastic band.

7. An acupressure pillow according to claim 1, wherein the pressure members of a pressure assembly are maintained a predetermined minimum distance apart from one another.

8. An acupressure pillow according to claim 7, wherein the pressure members are maintained a predetermined minimum distance apart from one another by at least one of:
   a spacer block disposed between the pressure members;
   a portion of the cushion material;
   or
   a guide.

9. An acupressure pillow according to claim 1, further comprising:
   a guide that restricts movement of the pressure members of a pressure assembly in at least one direction.

10. An acupressure pillow according to claim 9, wherein the guide comprises a track.

11. An acupressure pillow according to claim 10, wherein the track is one of:
    a linear flat track;
    a curved flat track; or
    an upwardly curved track.

12. An acupressure pillow according to claim 1, wherein one of:
    the pressure members are placed such that a portion of each pressure member extends above a nominal top surface of the cushion material; or
    the pressure members are placed such that no portion of the pressure members extends above the nominal top surface of the cushion material.

13. An acupressure pillow according to claim 1, wherein a pressure assembly is removably installed in the cushion material.

14. An acupressure pillow according to claim 1, wherein the at least one pressure assembly comprises a plurality of pressure assemblies.

15. An acupressure pillow according to claim 14, wherein at least two pressure assemblies have different sized pressure members.

16. An acupressure pillow according to claim 14, wherein the pressure members of at least two pressure assemblies are placed at different depths relative to a surface of the cushion material.

\* \* \* \* \*